US00PP08183P

United States Patent [19]

Carruth

[11] Patent Number: Plant 8,183

[45] Date of Patent: Mar. 23, 1993

[54] HYBRID FLORIBUNDA ROSE PLANT NAMED WEKUZ

[75] Inventor: Thomas F. Carruth, Altadena, Calif.

[73] Assignee: Weeks Wholesale Rose Grower, Inc., Upland, Calif.

[21] Appl. No.: 748,654

[22] Filed: Aug. 22, 1991

[51] Int. Cl.[5] ..... A01H 5/00

[52] U.S. Cl. ..... Plt./27

[58] Field of Search ..... Plt./22, 26, 27

*Primary Examiner*—Howard J. Locker

*Attorney, Agent, or Firm*—Christie, Parker & Hale

[57] ABSTRACT

A new variety of Floribunda rose suitable for garden decoration, having flowers of rose pink coloration.

1 Drawing Sheet

BACKGROUND OF THE INVENTION

This invention relates to a new and distinct variety of hybrid Floribunda rose. The plant is bushy, compact, rounded, and suitable for outdoor garden decoration. The new variety has as its seed parent an unnamed, unpatented red hybrid tea seedling and as its pollen parent the rose known as 'Bridal Pink', (U.S. Plant Pat. No. 2,851). The varietal denomination of the new variety is 'Wekuz'.

SUMMARY OF THE INVENTION

Among the features which distinguish the new variety Wekuz from other presently available commercial rose cultivars are the following combination of characteristics: abundant production of large well-formed flowers on a low compact plant habit, long-lived flowers of a relatively uniform and lasting old-rose pink coloration essentially as described and illustrated herein, and generally consistent performance in a wide range of climatic variation. Wekuz may be propagated by cuttings, budding, grafting, and tissue culture.

Asexual propagation of the new variety as performed in Kern County and Upland, Calif., shows that the foregoing and other distinguishing characteristics come true to form and are established and transmitted through succeeding propagations.

COMPARISON WITH PARENT VARIETIES

The new rose may be distinguished from its seed parent by the following combination of characteristics: whereas Wekuz is classed as a Floribunda, the seed parent is classed as a hybrid tea. Wekuz produces flowers of a deep pink coloration essentially as described and illustrated herein, whereas the seed parent produces flowers of a deep red coloration. The seed parent is a tall upright plant in habit, whereas the new cultivar has a significantly shorter rounded plant habit.

The new variety may be distinguished from its pollen parent by the following combination of characteristics: wherein Wekuz produces flowers of a deep pink coloration essentially as described and illustrated herein, Bridal Pink bears flowers of a significantly lighter pink coloration. Wekuz produces flower buds that are pointed yet ovoid in shape and of medium length, whereas the flower buds of Bridal Pink are significantly longer and more pointed in shape. Whereas Bridal Pink has a distinguishable fragrance, the new seedling bears only a very light fragrance.

BRIEF DESCRIPTION OF THE ILLUSTRATION

The accompanying photograph illustrates the plant in color and shows the flowering thereof from bud to full bloom depicted in color as nearly correct as it is possible to make in a color illustration of this character. Throughout this specification, color names and values are based upon the Colour Chart of The Royal Horticultural Society of London, England, except where common terms of color definition are employed.

DESCRIPTION OF THE NEW VARIETY

The following description pertains to rose plants of the new cultivar grown outdoors in August, 1991 in Upland, Calif. Phenotype may vary with differences in conditions of soil and climate.

FLOWER

The new variety bears its flowers sometimes singly, but usually three to four or more per stem. Flowers are usually borne in irregular rounded clusters on normal, short to medium length stems for the class. Outdoors, the plant blooms very abundantly and nearly continuously during the growing season. The flowers have a very slight tea fragrance.

BUD

The peduncle is of short to average length for the class, of average caliper, and usually erect. It is usually smooth, with few stipitate glands. Peduncle color is near to between Yellow-Green 146C and Green 138A, with an occasional blush of near Greyed-Purple 183C.

Before the calyx breaks, the bud is of medium to large size for the class, moderately short in length, and pointed to ovoid in shape. The surface of the bud bears some stipitate glands, usually with slender foliaceous parts extending beyond the tip of the bud equal to about ¼ or more of its length. Bud color is near to between Yellow-Green 146C and Green 138A.

The inner surface of the sepals has fine wooly tomentum; sepal margins are lined with some stipitate glands and numerous hairs.

As the first petal opens, the bud is somewhat medium to large for the class, moderately short to medium length, and somewhat pointed to ovoid in form. The color of the outside surface of the newly opened petals is near to between Red-Purple 64C and Red-Purple 58C. The color of the inside surface of the newly opened petals is near to between Red-Purple 64D and Red-Purple 58D. The bud opens well and is not prevented from opening by wet, cold, hot or dry weather.

BLOOM

When fully open, the bloom is moderately large for the class, ranging from 8 to 10 cms. in diameter. Petalage is double with 25 to 30 petals and 1 to 5 petaloids arranged irregularly. When partially open, the bloom form is moderately cupped to high centered, and the petals are somewhat cupped to undulated with petal edges somewhat rolled outward. When fully open, the bloom form is moderately more cupped to full, and the petals are somewhat more loosely cupped to undulated with petal edges moderately reflexed outward.

PETALS

The petals are of a moderately heavy crisp substance and of moderate thickness, with inside surfaces somewhat satiny to velvety and outside surfaces moderately shiny to satiny. The outside petals are nearly round to broadly obovate in shape with apices very rounded. The inside petals are more nearly ovate to obovate in shape with apices moderately rounded.

The following description and color values are from observation of flowers on a plant grown outdoors in Upland, Calif. in the month of August. Colors may be modified by being washed or shaded with other colors.

NEWLY OPENED FLOWER

The outside surface of the outside, intermediate and inner petals is near to between Red-Purple 64C and Red-Purple 58C.

The inside surface of the outside petals is near to between Red-Purple 65A and Red 55C. The inside surface of the intermediate petals is near to between Red-Purple 64D and Red-Purple 58D with some fading toward the petal edges of near to between Red-Purple 65A and Red 55C. The inside surface of the inner petals is near to between Red-Purple 64D and Red-Purple 58D.

The general color effect of the newly opened flower is between Red-Purple 64D and Red-Purple 58D.

THREE DAY OLD FLOWER

The outside surface of the outside and inner petals is near to between Red-Purple 64D and Red-Purple 58D.

The inside surface of the outside petals is near to between Red-Purple 65A and Red 56A. The inside surface of the inner petals is near to between Red-Purple 65A and Red 55C.

The general color effect of the three day old flower is near to between Red-Purple 65A and Red 55C.

On the spent bloom, the petals usually persist, fading to near to between Red-Purple 65C and Red 56B.

In August, blooms on the bush growing in the garden generally last from four to five or more days. Cut roses grown outdoors and kept at normal indoor living temperatures generally last five or more days.

MALE REPRODUCTIVE ORGANS

Stamens are average to many in number and are arranged regularly about the pistil. The filaments are of medium length, most with anthers. The anthers are of average size for the class and all open approximately at the same time. Anther color is near Greyed-Orange 167C when immature and near Brown 200C at maturity. Pollen is moderate to abundant and near Yellow-Orange 22D in color.

FEMALE REPRODUCTIVE ORGANS

Pistils are average in number (approximately 60). The styles are somewhat uneven, moderately short to average in length, somewhat thin to average in caliper, and somewhat loosely bunched. Stigma color is near Yellow 13D. Ovaries are usually all enclosed in the calyx.

Hips on this variety when grown in Upland, Calif. are of somewhat short to average in length, ovoid to globular in form, and near Greyed-Orange 168C in color when ripe. The hip surface is very smooth with moderately thick fleshy walls. The sepals fall away soon. Seeds are somewhat average in number (approximately 12 to 15), and usually medium in size.

FOLIAGE

The compound leaves are usually comprised of three to five leaflets and are borne abundantly. The leaves are moderately large for the class, somewhat heavy in texture, and somewhat matte in finish. The leaflets are shaped moderately oval to ovate with somewhat acute to acuminate apices and moderately round to acute bases. Their margins are usually irregularly serrate.

The upper surface of the mature leaf is near to between Green 136A and Yellow-Green 147A. The undersurface of the mature leaf is near to between Greyed-Green 194A and Yellow-Green 147B. The upper and undersurface of the young leaf is near to between Yellow-Green 146A and Yellow-Green 146B, sometimes lightly suffused more toward the leaf margin with near to between Greyed-Red 178A and Greyed-Purple 183A.

The rachis is average in caliper and moderately grooved with few stipitate glands on the edges of the upper side. The underside of the rachis is somewhat smooth with a few small prickles.

The stipules are short to medium in length with moderately narrow width somewhat short straight points that usually turn out at an angle of more than 45 degrees.

The plant displays an average degree of resistance to powdery mildew and blackspot as compared to other commercial varieties grown under comparable conditions in Upland, Calif.

GROWTH

The plant is bushy, compact, rounded, and of medium height habit for the class with very full branching. It displays very vigorous growth and the canes are of somewhat medium to heavy caliper for the class.

The major stems are near Yellow-Green 148D. They bear few large prickles which are medium length for the class. The prickles are almost straight with a medium length somewhat broad base; prickle color is near Greyed-Orange 165A. The major stem bears no small prickles and no hairs.

The branches are near to between Yellow-Green 147B and Green 137B. They bear some large and few small prickles which are medium length for the class. The prickles are almost straight with a medium length somewhat broad base; prickle color is near Greyed-Yellow 162C. There are no hairs.

The new shoots are near to between Yellow-Green 146A and Yellow-Green 146B, often moderately suffused with near to between Greyed-Red 178A and Greyed-Purple 183A. They bear several large and small prickles which are medium length for the class. They are almost straight with a medium length somewhat broad base; pirckle color is near Greyed-Purple 183C. There are no hairs.

I claim:

1. A new and distinct variety of Floribunda rose plant substantially as shown and described.

* * * * *

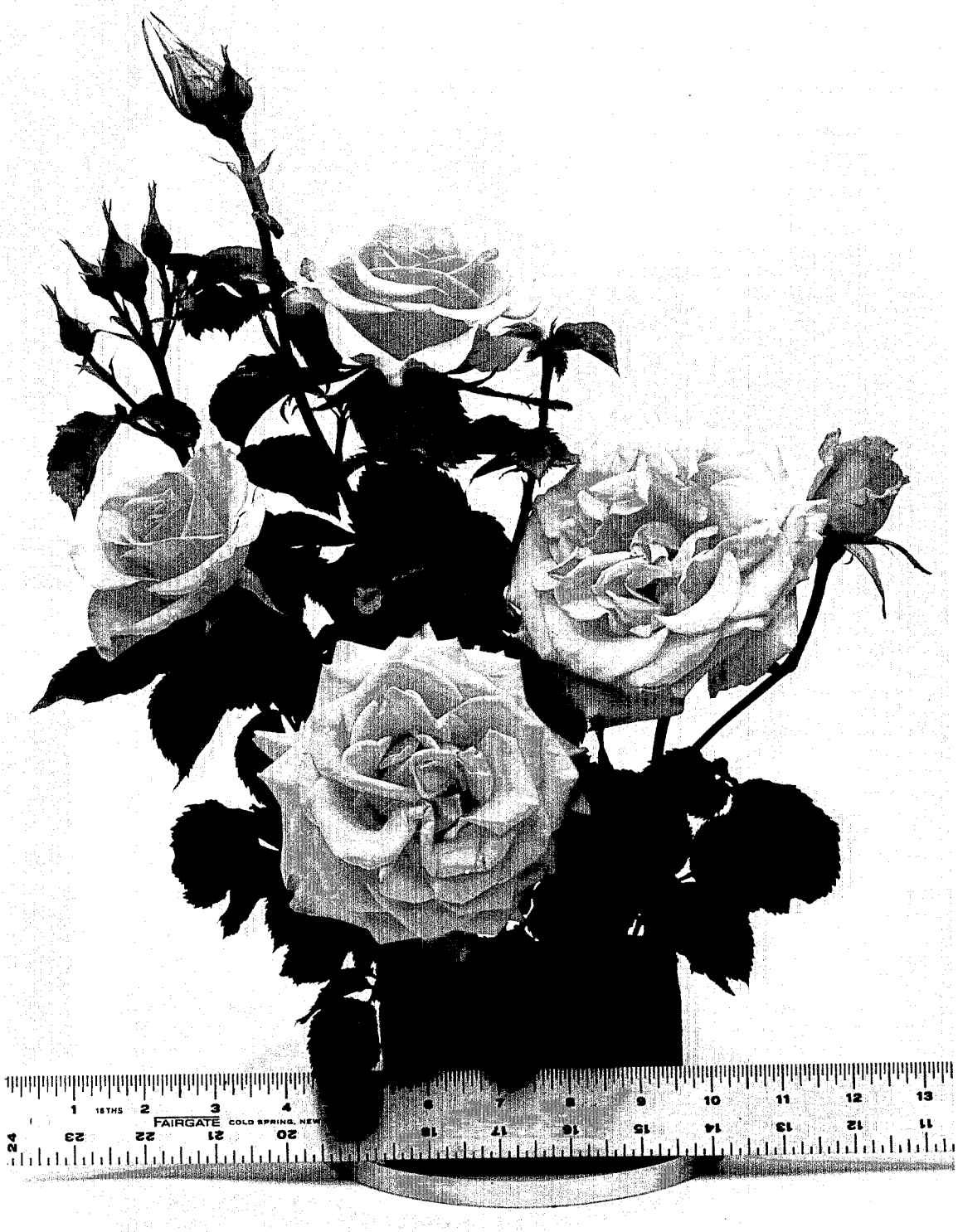
FAIRGATE